United States Patent
Masere et al.

(10) Patent No.: US 9,914,701 B2
(45) Date of Patent: Mar. 13, 2018

(54) USE OF STABLE LIPOPHILIC HYDROXYLAMINE COMPOUNDS FOR INHIBITING POLYMERIZATION OF VINYL MONOMERS

(71) Applicant: Ecolab USA Inc., St. Paul, MN (US)

(72) Inventors: Jonathan Masere, Richmond, TX (US); Andrew R. Neilson, Richmond, TX (US); Russell P. Watson, Houston, TX (US)

(73) Assignee: Ecolab USA Inc., St. Paul, MN (US)

( * ) Notice: Subject to any disclaimer, the term of this patent is extended or adjusted under 35 U.S.C. 154(b) by 0 days.

(21) Appl. No.: 15/072,780

(22) Filed: Mar. 17, 2016

(65) Prior Publication Data

US 2016/0272586 A1    Sep. 22, 2016

Related U.S. Application Data

(60) Provisional application No. 62/134,811, filed on Mar. 18, 2015.

(51) Int. Cl.
*C07D 211/94* (2006.01)
*C07C 7/20* (2006.01)

(52) U.S. Cl.
CPC .............. *C07D 211/94* (2013.01); *C07C 7/20* (2013.01)

(58) Field of Classification Search
CPC .................................................... C07D 211/94
USPC ......................................................... 546/242
See application file for complete search history.

(56) References Cited

U.S. PATENT DOCUMENTS

| | | |
|---|---|---|
| 2,455,745 A | 12/1948 | Erickson |
| 2,783,271 A | 2/1957 | Eck et al. |
| 2,810,651 A | 10/1957 | Thompson |
| 2,965,685 A | 12/1960 | Campbell |
| 3,222,334 A | 12/1965 | Demme |
| 3,320,305 A | 5/1967 | Wiese |
| 3,696,050 A | 10/1972 | Werts, III et al. |
| 3,704,235 A | 11/1972 | Rassat et al. |
| 4,202,742 A | 5/1980 | Castle |
| 4,293,347 A | 10/1981 | Haschke et al. |
| 4,487,981 A | 12/1984 | Miller et al. |
| 5,221,498 A | 6/1993 | Reid et al. |
| 5,235,056 A | 8/1993 | Cunkle et al. |
| 5,290,888 A | 3/1994 | Gatechair et al. |
| 5,426,257 A | 6/1995 | Arhancet |
| 5,489,720 A | 2/1996 | Arhancet |
| 5,648,574 A | 7/1997 | Arhancet et al. |
| 5,670,692 A | 9/1997 | Nesvadba et al. |
| 5,728,305 A | 3/1998 | Hawkinson |
| 5,728,872 A | 3/1998 | Riemenschneider |
| 5,750,765 A | 5/1998 | Nesvadba et al. |
| 5,773,674 A | 6/1998 | Arhancet et al. |
| 5,932,735 A | 8/1999 | Cunkle et al. |
| 6,180,231 B1 | 1/2001 | Keogh |
| 6,284,936 B2 | 9/2001 | Shahid |
| 6,342,647 B1 | 1/2002 | Roof et al. |
| 6,500,982 B1 | 12/2002 | Hale et al. |
| 6,525,146 B1 | 2/2003 | Shahid |
| 6,599,326 B1 | 7/2003 | Seltzer et al. |
| 6,686,422 B2 | 2/2004 | Shahid |
| 6,770,222 B1 | 8/2004 | Ukita et al. |
| 7,066,990 B2 | 6/2006 | Wood et al. |
| 7,132,540 B1 | 11/2006 | Jawdosiuk et al. |
| 7,282,136 B2 | 10/2007 | Howdeshell |
| 7,309,682 B2 | 12/2007 | Lupia et al. |
| 7,429,545 B2 | 9/2008 | Lupia et al. |
| 7,618,644 B2 | 11/2009 | Lupia et al. |
| 7,718,096 B2 | 5/2010 | Yale et al. |
| 7,943,809 B2 | 5/2011 | Benage et al. |
| 8,110,650 B2 | 2/2012 | Nava et al. |
| 8,247,593 B2 | 8/2012 | Morrison et al. |
| 8,691,944 B2 | 4/2014 | Clark et al. |
| 8,884,038 B2 | 11/2014 | Masere |
| 2009/0287013 A1 | 11/2009 | Morrison et al. |
| 2010/0168434 A1 | 7/2010 | Loyns et al. |
| 2012/0056128 A1 | 3/2012 | Bauchet |
| 2012/0313036 A1 | 12/2012 | Masere |
| 2013/0178652 A1 | 7/2013 | Fruchey et al. |
| 2014/0288337 A1 | 9/2014 | Rinker et al. |

FOREIGN PATENT DOCUMENTS

| | | |
|---|---|---|
| CA | 2232502 | 9/1998 |
| CA | 2 260 310 A1 | 7/2000 |
| CN | 102795966 A | 11/2012 |
| DE | 102008061611 A1 | 6/2009 |
| EP | 0 373 636 A1 | 6/1990 |
| EP | 0 765 856 A1 | 4/1997 |

(Continued)

OTHER PUBLICATIONS

King, Med. Chem., Principle and Practice (1994), pp. 206-208.*
Miyazawa, T. et al., New Method for Preparation of Superoxide Ion by Use of Amino Oxide, J. Org. Chem., Dec. 1985, vol. 50, No. 25, pp. 5389-5391.
International Search Report relating to PCT Patent Application No. PCT/US2016/022731 dated Jun. 21, 2016, 6 pages.
Written Opinion relating to PCT Patent Application No. PCT/US2016/022731 dated Jun. 21, 2016, 7 pages.
Ma, Y., "Nitroxides in Mechanistic Studies: Ageing of Gold Nanoparticles and Nitroxide Transformation in Acids," Submitted to the Department of Chemistry, University of York, 2010, 221 pages.

(Continued)

*Primary Examiner* — Taofiq A Solola
(74) *Attorney, Agent, or Firm* — Senniger Powers LLP

(57) ABSTRACT

The present invention generally relates to compounds and methods for inhibiting the radical polymerization of unsaturated compounds, particularly vinyl monomers. More particularly, it relates to the use of stable hydroxyl amines to inhibit the polymerization of unsaturated compounds (e.g., vinyl monomers) wherein said stable hydroxylamine is soluble in organic solvents, particularly hydrocarbon solvents consisting of unsaturated and, therefore, polymerizable constituents.

12 Claims, No Drawings

(56) References Cited

FOREIGN PATENT DOCUMENTS

| EP | 0 915 108 A1 | 5/1999 |
|---|---|---|
| EP | 0 943 665 A1 | 9/1999 |
| WO | 01/12677 A1 | 2/2001 |
| WO | 01/40404 A1 | 6/2001 |
| WO | 2006/078123 A1 | 7/2006 |
| WO | 2007/045886 A1 | 4/2007 |
| WO | 2008/103613 A2 | 8/2008 |
| WO | 2015/084843 A1 | 6/2015 |

OTHER PUBLICATIONS

Sciannamea, V., et al., "In-Situ Nitroxide-Mediated Radical Polymerization (NMP) Processes: Their Understanding and Optimization," Chemical Reviews, 2008, pp. 1104-1126, vol. 108, No. 3.
Synthesis of Tropine & Its Derivatives, accessed from <http://www.lab-q.net/synthesis/syn_tropine> on Dec. 18, 2014, 6 pages.
Jurd, Leonard et al., New Types of Insect Chemosterilants, Benzylphenols and Benzl-1,3-benzodioxole Derivatives as Additives to Housefly Diet, Journal of Agricultural and Food Chemistry, 1979, pp. 1007-1016, vol. 27, No. 5.

\* cited by examiner

USE OF STABLE LIPOPHILIC HYDROXYLAMINE COMPOUNDS FOR INHIBITING POLYMERIZATION OF VINYL MONOMERS

CROSS-REFERENCE TO RELATED APPLICATION

This application claims priority to U.S. Provisional Patent Application Ser. No. 62/134,811 filed on Mar. 18, 2015, the disclosure of which is incorporated herein by reference in its entirety.

FIELD OF THE INVENTION

The present invention generally relates to compounds and methods for inhibiting the radical polymerization of unsaturated compounds, particularly vinyl monomers. More particularly, it relates to the use of lipophilic N,N-disubstituted hydroxyl amines to inhibit the polymerization of unsaturated compounds (e.g., vinyl monomers) soluble in organic solvents, particularly hydrocarbon solvents.

BACKGROUND OF THE INVENTION

Unsaturated compounds, particularly vinyl monomers, can undesirably polymerize at various stages of their manufacture, processing, handling, storage, and use. Vinyl monomers can undergo self-initiated polymerization at elevated temperatures even in the absence of polymerization promoters. Thus, undesired thermal polymerization can be a problem during the purification of vinyl aromatic monomers and during sudden process shutdowns. Undesirable polymerization results in product loss because the valuable monomer end product is consumed in the undesired side reaction. Moreover, polymerization reduces production efficiency as the polymer is deposited on process equipment. This fouling of process equipment may require a shutdown to remove the undesired polymer by physical methods.

The stable free radical, 4-hydroxy-2,2,6,6-tetra-methylpiperidinoxy (HTEMPO), has been used extensively to control free radical polymerization of reactive monomers during the purification, handling, transportation and storage. However, to improve its efficacy as an inhibitor, there are two alternatives. Firstly, the dose of HTEMPO can be increased. However, as the concentration is increased, the dissolved HTEMPO will crystallize especially if the ambient temperature under which the solution is used or stored falls. HTEMPO can also crystallize if the solvency of the hydrocarbon media decreases, for instance, a solution comprising aromatic solvents will have a lower solvency when it comes into contact with aliphatic media. Owing to the low solubility of HTEMPO in aliphatic media, the introduction of an aromatic-based solvent of HTEMPO will result in the precipitation of HTEMPO thereby resulting in the plugging of quills and transfer lines.

Secondly, the conversion of HTEMPO to its hydroxylamine, HTEMPOL, is the other alternative to increasing its polymer inhibiting efficiency. Unlike HTEMPO that is soluble in aromatic hydrocarbon solvents, HTEMPOL is sparingly soluble in hydrocarbon solvents. In applications that involve aqueous media, the water-soluble HTEMPOL can be used with nominal risk of precipitation whereas it will precipitate in hydrocarbon media. Consequently, the use of HTEMPOL as an inhibitor is restricted to stopping premature polymerization in aqueous media.

In prior art, hydrocarbon-soluble hydroxylamines have been used as inhibitors. Due to the presence of hydrogen substituents of the a-carbon atoms relative to the hydroxylamine functional group, said hydroxylamines are therefore unstable. At high operational temperatures associated with the purification and other processes involving vinylic monomers, these unhindered or partially hindered hydroxylamines decompose to yield contaminant byproducts, namely; aldehydes and primary hydroxylamines. As an example, N,N-diethylhydroxylamine will decompose to acetaldehyde and ethylhydroxylamine.

More particularly, this invention addresses inhibition of polymerization in units typically associated with hydrophobic vinylic monomers such as in distillation towers where aqueous-based inhibitors are not very effective or the poor solubilities of the highly polar inhibitors result in the precipitation or recrystallization of said inhibitors when mixed with hydrocarbon media. In equipment in which a hydrocarbon phase is in contact with an aqueous phase, the currently used hydrophilic hydroxylamines preferentially partition into the aqueous phase rather than the hydrocarbon phase. By contrast, the organic-soluble vinylic species that are liable to polymerization partition into the hydrocarbon phase. Owing to this partitioning tendency, the prior art hydroxylamines are not effective polymerization inhibitors.

Thus, a need exists for a hydrocarbon soluble, stable free-radical scavenger.

SUMMARY OF THE INVENTION

One aspect of the present invention is a hydroxylamine compound having the structure of Formula 1:

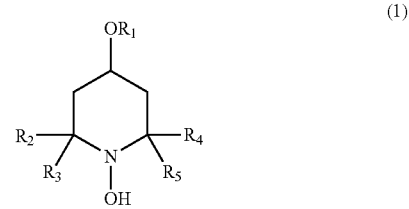

wherein $R_1$ is alkyl, aryl, alkaryl, heterocyclo, or —C(O)$R_6$; $R_2$, $R_3$, $R_4$, and $R_5$, are independently selected from the group consisting of alkyl, alkylaryl, aryl, heteroaryl, or $R_2$ and $R_3$ or $R_4$ and $R_5$ together can form a spiro ring; and $R_6$ is alkyl, alkylaryl, aryl, or heteroaryl.

Another aspect of the invention is a hydroxylamine oligomer having the structure of Formula 2:

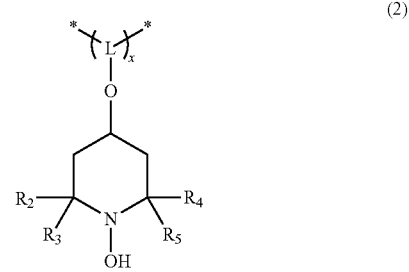

wherein L is a linker comprising alkylene, arylene, alkarylene, heterocyclo, or diacyl; $R_2$, $R_3$, $R_4$, and $R_5$, are independently alkyl, alkylaryl, aryl, heteroaryl, or $R_2$ and $R_3$ or $R_4$ and $R_5$ together can form a spiro ring; and x is an integer greater than 2.

Yet another aspect of the invention is a hydroxylamine dimer compound having the structure of Formula 3:

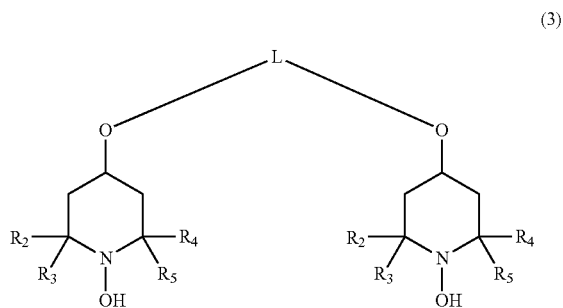

(3)

wherein L is a linker comprising alkylene, arylene, alkarylene, heterocyclo, or diacyl; and $R_2$, $R_3$, $R_4$, and $R_5$, are independently alkyl, alkylaryl, aryl, heteroaryl, or $R_2$ and $R_3$ or $R_4$ and $R_5$ together can form a spiro ring.

Yet another aspect of the invention is a method for inhibiting polymerization of an unsaturated compound comprising an unsaturated carbon-carbon bond comprising contacting the unsaturated compound with the hydroxylamine compound of Formula 1 or the hydroxylamine dimer compound of Formula 2.

Other objects and features will be in part apparent and in part pointed out hereinafter.

DESCRIPTION OF THE PREFERRED EMBODIMENTS

In place of hydroxylamines that are insoluble in hydrocarbon media and that are unstable at high process temperatures, hydrocarbon-soluble and stable hydroxylamines are disclosed as more efficient scavengers of free radical species that cause unwanted polymerization in hydrocarbon media. Alternative hydroxylamines that are preferentially soluble in hydrocarbon media and not prone to decomposing to contaminants can be used either as stand-alone inhibitors or in combination with other polymerization-inhibiting compounds. These compounds and combinations show highly effective polymer inhibition efficacy.

The present invention is directed to hydroxylamine compounds, hydroxylamine oligomeric compounds, and methods of use of the hydroxylamine and hydroxylamine oligomeric compounds for inhibiting polymerization of an unsaturated compound comprising an unsaturated carbon-carbon bond in hydrocarbon streams. The unsaturated compound is in contact with an effective amount of a hydroxylamine compound of Formula 1 or a hydroxylamine oligomer of Formula 2 or a dimer compound of Formula 3. Unsaturated hydrocarbons are reactive and liable to undesirable polymerization under typical processing, transportation and storage conditions. The undesired polymerization of the unsaturated compounds is costly due to the resultant loss of the desired monomer product. Thus, methods for inhibiting this unwanted polymerization are beneficial for said hydrocarbon processes.

The hydroxylamines of Formulae 1, 2, and 3 are stable to decomposition at temperatures they are typically exposed to during processing of the unsaturated compounds where they are acting as polymerization inhibitors. The hydroxylamines of Formulae 1, 2, and 3 are also soluble in the hydrocarbons at the concentrations effective for this method. This means that they do no precipitate or crystallize in the system.

One aspect of the invention is a hydroxylamine compound having the structure of Formula 1:

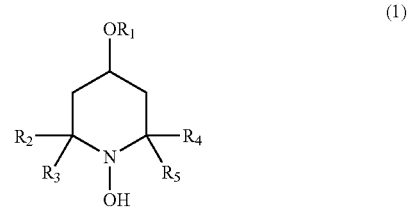

(1)

wherein $R_1$ is alkyl, aryl, alkaryl, heterocyclo, or —C(O)$R_6$; $R_2$, $R_3$, $R_4$, and $R_5$, are independently selected from the group consisting of alkyl, alkylaryl, aryl, heteroaryl, or $R_2$ and $R_3$ or $R_4$ and $R_5$ together can form a spiro ring; and $R_6$ is alkyl, alkylaryl, aryl, or heteroaryl.

Another aspect of the invention is a hydroxylamine oligomer having the structure of Formula 2:

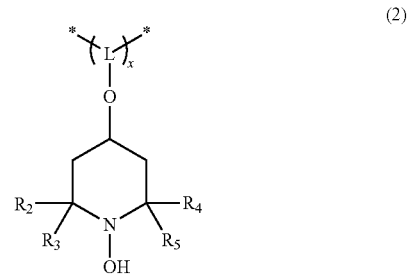

(2)

wherein L is a linker comprising an alkylene, arylene, alkarylene, heterocyclo, or diacyl; $R_2$, $R_3$, $R_4$, and $R_5$ are independently selected from the group consisting of alkyl, alkylaryl, aryl, heteroaryl, or $R_2$ and $R_3$ or $R_4$ and $R_5$ together can form a spiro ring; $R_6$ is alkyl, alkylaryl, aryl, heteroaryl; and x is an integer greater than 2.

Yet another aspect of the invention is a hydroxylamine dimer compound having the structure of Formula 3:

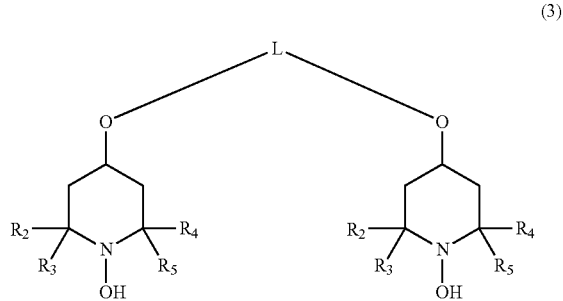

(3)

wherein L is a linker comprising an alkylene, arylene, alkarylene, heterocyclo, or diacyl; $R_2$, $R_3$, $R_4$, and $R_5$, are independently selected from the group consisting of alkyl, alkylaryl, aryl, heteroaryl, or $R_2$ and $R_3$ or $R_4$ and $R_5$ together can form a spiro ring.

A further aspect of the invention is a method for inhibiting polymerization of an unsaturated compound comprising an unsaturated carbon-carbon bond comprising contacting the unsaturated compound with the hydroxylamine compound of Formula 1 or the hydroxylamine dimer compound of Formula 2.

For the compounds of Formulae 1 and 2 and their use in the methods described herein, $R_1$ can be an alkyl, or alkylaryl group of from about 1 to about 18 carbon atoms.

Further, the compounds of Formulae 1 and 2 and the methods described herein, can have $R_1$ be propyl, butyl, pentyl, or hexyl. Preferably, $R_1$ can be n-butyl, sec-butyl, isobutyl, or tert-butyl.

Also, the compounds of Formulae 1 and 2 can have $R_1$ be $C_1$-$C_{18}$ alkaryl. Preferably, $R_1$ is benzyl.

Further, for the compounds of Formulae 1 and 2 and their use in the methods described herein, $R_2$, $R_3$, $R_4$, and $R_5$, can independently be $C_1$-$C_9$ alkyl. Preferably, $R_2$, $R_3$, $R_4$, and $R_5$, can independently be $C_1$-$C_3$ alkyl.

Additionally, for the compounds of Formulae 1 and 2, $R_2$, $R_3$, $R_4$, and $R_5$, can independently be haloalkyl.

The compounds of Formulae 1 and 2 can have $R_1$ be n-butyl and $R_2$ $R_3$, $R_4$, and $R_5$ be methyl.

Alternatively, compounds of Formulae 1 and 2 can have $R_1$ be benzyl and $R_2$ $R_3$, $R_4$, and $R_5$ be methyl.

For the compound of Formula 1, $R_6$ can be alkyl; preferably, $R_6$ can be methyl, ethyl, propyl, or butyl.

For the polymer or oligomer of Formula 2, x can be from 2 to 100; from 2 to 50; or from 2 to 10.

For the polymer or oligomer of Formula 2, x is selected so that the polymer or oligomer of Formula 2 does not precipitate or crystallize in a hydrocarbon stream.

For the methods of inhibiting polymerization using the hydroxylamine compound of Formula 1 or the hydroxylamine dimer compound of Formula 2, the unsaturated compound can be a vinyl monomer.

Further, the unsaturated compound can be ethylene, propylene, acetylene, styrene, vinyl chloride, vinyl alcohol, vinyl acetate, acrylonitrile, acrylate esters, methacrylate esters, acrylic acid, (meth)acrolein, acrolein, butadiene, indene, divinylbenzene, isoprene, acetylene, vinyl acetylene, cyclopentadiene, or a combination thereof. Preferably, the unsaturated compound can comprise acrylate esters, methacrylate esters, styrene, or a combination thereof.

The polymerization inhibition method can stabilize and inhibit polymerization of an unsaturated compound during a manufacture, a purification, transportation or a storage process.

The polymerization inhibition method can also stabilize and inhibit polymerization of an unsaturated compound in a primary fractionation process, light ends fractionation, non-aromatic halogenated vinyl fractionation, process-gas compression, butadiene extraction, propane dehydrogenation, diesel and petrol fuel stabilization, olefin metathesis, styrene purification, hydroxyhydrocarbon purification, or delays the polymerization of resins and compositions comprising ethylenically unsaturated species. Preferably, the polymerization inhibition method can stabilize and inhibit polymerization of an unsaturated compound in a butadiene extraction or styrene purification.

Preferably for the hydroxylamine compounds of Formula 1, $R_1$ is n-butyl or benzyl and $R_2$, $R_3$, $R_4$, and $R_5$ are methyl. These compounds have the structures:

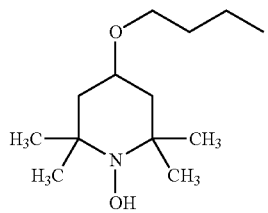 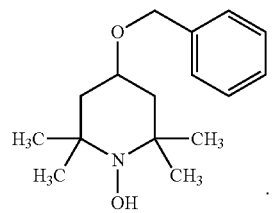

Methods for preparing compounds of Formulae 1 and 2 are well known in the art and will be apparent to the skilled person. As an illustrative example, 4-alkoxy-2,2,6,6-tetramethyl-1-piperidinols are prepared. This is achieved in a two-step process starting with commercially available 4-hydroxy-TEMPO. In the first step, 4-OH-TEMPO is reacted with an alkylating agent (e.g., n-butyl bromide or benzyl chloride) in the presence of base to give the corresponding 4-alkoxy TEMPO derivative. In the second step, the nitroxide radical is treated with a reducing agent, (e.g., hydrazine hydrate or N,N-diethylhydroxylamine) to give a 4-alkoxy TEMPO hydroxylamine (4-alkoxy TEMPOH).

Another aspect of the invention is a composition comprising a compound of Formula 1 and a solvent. Suitable organic solvents include pentane, heptane, hexane, benzene, ethylbenzene, toluene, or a combination thereof. The solvents are not restricted to the above-mentioned examples.

The composition can comprise one or more additional polymerization inhibitors. Compounds that are suitable as additional polymerization inhibitors in the inventive composition include phenols, alkylated phenols, nitrophenols, nitrosophenols, quinones, hydroquinones, quinone ethers, quinone methides, amines, hydroxylamines, and phenothiazines.

The polymerization inhibitor compositions described herein can be introduced into the monomer to be protected by any conventional method. It can be added as a concentrate solution in suitable solvents just upstream of the point of desired application by suitable means. In addition, these compounds can be injected separately into the distillation train with the incoming feed, or through separate entry points providing efficient distribution of the inhibitor composition. Since the inhibitor is gradually depleted during operation, it is generally necessary to maintain the appropriate amount of the inhibitor in the distillation apparatus by adding inhibitor during the course of the distillation process. This addition may be carried out either on a generally continuous basis or by intermittently charging inhibitor into the distillation system if the concentration of inhibitor is to be maintained above the minimum required level.

The effective amount of a compound of Formulae 1, 2, and 3 can be from about 0.1 mmolal to 5 mmolal; preferably, from about 0.2 mmolal to about 2 mmolal.

The compounds of Formula 1 can be prepared by adding 4-hydroxy-2,2,6,6-tetraalkylpiperidin-1-oxyl to a non-protic polar solvent such as tetrahydrofuran (THF). Then, to the resultant solution, a base was added followed by stirring of the mixture at room temperature. Then, a solution of an alkyl halide in a non-protic polar solvent such as THF was added dropwise into the flask. The reaction mixture was heated until the reaction was completed. Deionized water was added and the layers separated. The organic fraction was isolated, dried over anhydrous magnesium sulfate, and the solvent removed in vacuo. This product was added to an aromatic solvent such as toluene and a reducing agent, such as hydrazine hydrate was added and the mixture was heated.

Then, the reaction was cooled and washed with water. The organic fraction was isolated, dried over anhydrous magnesium sulfate, and the solvent removed in vacuo to give 4-alkoxy-2,2,6,6-tetraalkylpiperidin-1-ol.

To prepare oligomers and dimers of Formulae 2 and 3, the alkyl halide can be substituted with an alkyl dihalide or another reactant having two or more reactive groups. Additionally, a polymer having a reactive group could be used to react with the adding 4-hydroxy-2,2,6,6-tetraalkylpiperidin-1-oxyl to form a polymer of Formula 2.

Unless otherwise defined herein, "TEMPO" refers to 2,2,6,6-tetramethylpiperidin-1-oxyl.

"4-OH-TEMPO" refers to 4-hydroxy-TEMPO, otherwise known as 4-hydroxy-2,2,6,6-tetramethylpiperidin-1-oxyl or TEMPOL.

"4-OH-TEMPOH" refers to 4-hydroxy-TEMPO hydroxylamine, otherwise known as 2,2,6,6-tetramethylpiperidin-1,4-diol.

"4-Bu-TEMPOH" refers to 4-butoxy-TEMPO hydroxylamine, otherwise known as 4-butoxy-2,2,6,6-tetramethyl-1-piperidinol.

"4-Bn-TEMPOH" refers to 4-benzyloxy TEMPO hydroxylamine, otherwise known as 4-benzyloxy-2,2,6,6-tetramethyl-1-piperidinol.

Unless otherwise indicated, an alkyl group as described herein alone or as part of another group is an optionally substituted linear saturated monovalent hydrocarbon substituent containing from one to sixty carbon atoms and preferably one to thirty carbon atoms in the main chain or eight to thirty carbon atoms in the main chain, or an optionally substituted branched saturated monovalent hydrocarbon substituent containing three to sixty carbon atoms, and preferably eight to thirty carbon atoms in the main chain. Examples of unsubstituted alkyl groups include methyl, ethyl, n-propyl, i-propyl, n-butyl, i-butyl, s-butyl, t-butyl, n-pentyl, i-pentyl, s-pentyl, t-pentyl, and the like.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl, bicyclo[2.2.2] octanyl and the like. Representative cycloalkyl groups include cyclopropyl, cyclobutyl, cyclopentyl, cyclohexyl, bicyclo[2.2.1] heptanyl, bicyclo[2.2.2] octanyl, and the like.

The terms "aryl" or "ar" as used herein alone or as part of another group (e.g., aralkyl or alkaryl) denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl. The term "aryl" also includes heteroaryl.

The term "substituted" as in "substituted aryl," "substituted alkyl," and the like, means that in the group in question (i.e., the alkyl, aryl or other group that follows the term), at least one hydrogen atom bound to a carbon atom is replaced with one or more substituent groups such as hydroxy (—OH), alkylthio, phosphino, amido (—CON($R_A$)($R_B$), wherein $R_A$ and $R_B$ are independently hydrogen, alkyl, or aryl), amino(—N($R_A$)($R_B$), wherein $R_A$ and $R_B$ are independently hydrogen, alkyl, or aryl), halo (fluoro, chloro, bromo, or iodo), silyl, nitro (—$NO_2$), an ether (—$OR_A$ wherein $R_A$ is alkyl or aryl), an ester (—OC(O)$R_A$ wherein $R_A$ is alkyl or aryl), keto (—C(O)$R_A$ wherein $R_A$ is alkyl or aryl), heterocyclo, and the like. When the term "substituted" introduces a list of possible substituted groups, it is intended that the term apply to every member of that group. That is, the phrase "optionally substituted alkyl or aryl" is to be interpreted as "optionally substituted alkyl or optionally substituted aryl."

"Alkaryl" means an aryl group attached to the parent molecule through an alkylene group. The number of carbon atoms in the aryl group and the alkylene group is selected such that there is a total of about 6 to about 18 carbon atoms in the alkaryl group. A preferred alkaryl group is benzyl.

"Haloalkyl" refers to an alkyl group as defined herein wherein one of more hydrogen atoms on the alkyl group have been substituted with a halogen. Representative haloalkyl groups include flouromethyl, difluoromethyl, trifluoromethyl, fluoroethyl, difluoroethyl, trifluoroethyl, tetrafluoroethyl, perfluoroethyl, and the like.

"Vinyl monomer" refers to a monomer comprising at least one carbon-carbon double bond. The monomer can be substituted with various groups, such as acids (e.g., acrylic acid), esters (e.g., acrylate esters), halogen (e.g., vinyl chloride), aryl (e.g., styrene, vinyl toluene, divinylbenzene), cyano (e.g., acrylonitrile), and acetoxy (e.g., vinyl acetate). The monomer can be conjugated (e.g., butadiene, cyclopentadiene, vinyl acetylene, indene, and the like).

A polymerization "inhibitor" refers to a composition of matter that is able to scavenge radicals in a radical polymerization process. Inhibitors can be used to stabilize monomers and prevent their polymerization or quench polymerization when a desired conversion is achieved. They can also be used to regulate or control the kinetics of a polymerization process.

Having described the invention in detail, it will be apparent that modifications and variations are possible without departing from the scope of the invention defined in the appended claims.

EXAMPLES

The foregoing may be better understood by reference to the following examples, which are presented for purposes of illustration and are not intended to limit the scope of the invention.

All reactions were performed under an atmosphere of nitrogen unless stated otherwise. The reagents 4-hydroxy-TEMPO, potassium tert-butoxide, 1-bromobutane, and benzyl chloride were purchased from Sigma-Aldrich.

Example 1

Synthesis of
4-butoxy-2,2,6,6-tetramethylpiperidin-1-ol
(4-Bu-TEMPOH)

To a round-bottomed flask equipped with a stir bar was added 4-hydroxy-2,2,6,6-tetramethylpiperidin-1-oxyl ("4-hydroxy-TEMPO", 26.2 g, 152 mmol) and 700 mL of tetrahydrofuran (THF). To the resultant solution, 20.5 g of potassium tert-butoxide (20.5 g, 183 mmol) was added followed by stirring of the mixture at room temperature for two hours. After two hours, a solution of 25.0 g (182 mmol) of 1-bromobutane in 100 mL of THF was added dropwise into the flask. The reaction mixture was refluxed overnight for an approximate duration of 21 hours, then cooled. Deionized water was added and the layers separated. The organic fraction was isolated, dried over anhydrous magnesium sulfate, and the solvent removed in vacuo. The residue was taken up in a minimum amount of dichloromethane and chromatographed on 100 g of silica gel using as the mobile phase 20% ethyl acetate/hexane. The total yield of 4-butoxy-TEMPO was 4.99 g (38%).

To a 250 mL one-neck round-bottomed flask equipped with a stir bar was added a solution of 4-butoxy-TEMPO (4.852 g, 21.26 mmol) in 100 mL of toluene. To this solution was added hydrazine hydrate (1.03 mL, 21.26 mmol), then the reaction mixture was heated at reflux. After one hour, the reaction mixture was cooled to 25° C., and washed with deionized water. The organic fraction was isolated, dried over anhydrous magnesium sulfate, and the solvent removed in vacuo to give 4-butoxy-2,2,6,6-tetramethylpiperidin-1-ol (4-Bu TEMPOH) in a yield of 81%. The structure of the product was confirmed by $^1$H-NMR and $^{13}$C-NMR.

Example 2

Synthesis of
4-benzyloxy-2,2,6,6-tetramethylpiperidin-1-01
(4-Bn-TEMPOH)

To a round-bottomed flask equipped with a stir bar was added 4-hydroxy-2,2,6,6-tetramethylpiperidine 1-oxyl ("1-hydroxy-TEMPO", 10.0 g, 58.1 mmol) and 300 mL of dry tetrahydrofuran (THF). To the resultant solution, 7.9 g (70.4 mmol) of potassium tert-butoxide was added. After stirring for two hours at room temperature, a solution of benzyl chloride (8.1 g, 64.0 mmol) in 100 mL of dry THF was added drop wise over 45 minutes while the system was heated at reflux. After the addition was complete and after a total of 7 hours at reflux, heating was stopped, and the system was allowed to cool and stirred at room temperature overnight. Deionized water (100 mL) was added and the layers were separated. The aqueous phase was extracted three times with 25 mL portions of ethyl acetate. The combined organic phases were washed with a mixture of 100 mL water and 80 mL brine before drying over anhydrous magnesium sulfate. The solvents were removed by rotary evaporation, and the residue was taken up in 25 mL dichloromethane and chromatographed on 120 g of silica gel using as the mobile phase 20% ethyl acetate/hexane. The yield of pure eluted product was 5.39 g (35%), and the impure solid isolated from other fractions was recrystallized from cold hexane, affording material that resulted in an overall yield of 12.03 g (79%) of pure 1-benzyloxy-TEMPO.

1-Benzyloxy-TEMPO (1.001 g, 3.82 mmol) was dissolved in n-hexane to give an orange-colored solution. To this solution was added a stoichiometric excess of N,N-diethylhydroxylamine (DEHA, 2 mL, 19.06 mmol) until the resulting solution turned pale yellow. The solution was washed with deionized water. After recovering and drying the organic layer with anhydrous magnesium sulfate, the solvent was removed to yield 4-benzyloxy-2,2,6,6-tetramethylpiperidin-1-ol (4-Bn-TEMPOH) in a yield of 45%. The structure of the product was confirmed by $^1$H-NMR and $^{13}$C-NMR.

Example 3

Polymerization of Methyl Methacrylate

Comparative Example 3A

Untreated Methyl Methacrylate

A solution consisting of 20 ppm of benzoyl peroxide in methyl methacrylate was prepared. Ten mL aliquots of this solution were added to each of twenty-four Ace Glass #15 threaded pressure tubes equipped with PTFE screw caps and fluoroelastomer (FETFE) O-rings. To purge dissolved oxygen, each solution was sparged with nitrogen for 2 minutes, after which the tube was immediately sealed and the solution kept under a nitrogen headspace. Polymerization reactions were carried out by loading the tubes into a heating block that had been preheated to 100° C. After 30 minutes, and every 15 minutes after that, four tubes were retrieved from the block and the polymerization reactions quenched by cooling the tubes in an ice bath. The cooled polymer solutions were immediately diluted with toluene. A proprietary method was used to measure the amount of polymer in the diluted analyte solutions.

Comparative Example 3B

Methyl Methacrylate Treated with
4-hydroxy-TEMPO (4-OH-TEMPO)

A solution consisting of 0.58 mmol of 4-hydroxy-TEMPO and 20 ppm of benzoyl peroxide in methyl methacrylate was prepared. Ten mL aliquots of this solution were added to each of twenty-four Ace Glass #15 threaded pressure tubes equipped with PTFE screw caps and fluoroelastomer (FETFE) O-rings. The procedure in Comparative Example 3A was used to remove oxygen, polymerize the solutions, and measure the amount of polymer formed.

Example 3C

Methyl Methacrylate Treated with
4-benzyl-2,2,6,6-tetramethylpiperidin-1-ol
(4-BnO-TEMPOH)

A solution consisting of 0.58 mmol of 4-benzyl-2,2,6,6-tetramethylpiperidin-1-ol and 20 ppm of benzoyl peroxide in methyl methacrylate was prepared. Ten mL aliquots of this solution were added to each of twenty-four Ace Glass #15 threaded pressure tubes equipped with PTFE screw caps and fluoroelastomer (FETFE) O-rings. The procedure in Comparative Example 3A was used to remove oxygen, polymerize the solutions, and measure the amount of polymer formed.

Example 3D

Methyl Methacrylate Treated with
4-butoxy-2,2,6,6-tetramethylpiperidin-1-ol
(4-BuO-TEMPOH)

A solution consisting of 0.58 mmol of 4-butoxy-2,2,6,6-tetramethylpiperidin-1-ol and 20 ppm of benzoyl peroxide in methyl methacrylate was prepared. Ten mL aliquots of this solution were added to each of twenty-four Ace Glass #15 threaded pressure tubes equipped with PTFE screw caps and fluoroelastomer (FETFE) O-rings. The procedure in Comparative Example 3A was used to remove oxygen, polymerize the solutions, and measure the amount of polymer formed.

The results of the experiments in Examples 3A-3D is summarized in Table 1:

TABLE 1

Inhibition of methyl methacrylate polymerization (initiated with 20 ppm benzoyl peroxide) at 100° C. under anaerobic conditions in the presence of no inhibitor (blank) or 0.58 mmol of inhibitor.

| | Poly(methyl methacrylate) (ppm) | | | |
|---|---|---|---|---|
| Time (min) | Ex. 3A Blank | Ex. 3B 4-OH-TEMPO | Ex. 3C 4-BnO-TMPOH | Ex. 3D 4-BuO-TMPOH |
| 30 | 18588 | 31 | 5 | 2 |
| 45 | 48550 | 34 | 4 | 2 |
| 60 | 80231 | 64 | 4 | 2 |
| 75 | 83625 | 93 | 4 | 3 |
| 90 | 93993 | 144 | 4 | 2 |
| 105 | | 180 | 3 | 5 |

Example 4

Polymerization of Styrene

Comparative Example 4A

Untreated Styrene

A disposable, prepacked alumina column was used to remove 4-tert-butylcatechol (TBC) from styrene. Nine mL aliquots of freshly de-inhibited styrene were charged into each of twenty-four Ace Glass #15 threaded pressure tubes equipped with PTFE screw caps and fluoroelastomer (FETFE) O-rings. To purge dissolved oxygen, each solution was sparged with nitrogen for 2 minutes, after which the tube was immediately sealed and the solution kept under a nitrogen headspace. Polymerization reactions were carried out by loading the tubes into a heating block that had been preheated to 120° C. After 30 minutes, and every 15 minutes after that, four tubes were retrieved from the block and the polymerization reaction quenched by cooling the tubes in an ice bath. The cooled polymer solutions were immediately diluted with toluene. The amount of polymer formed was determined by precipitation with methanol according to the ASTM D2121 method.

Comparative Example 4B

Styrene Treated with 4-hydroxy-TEMPO (4-OH-TEMPO)

A solution consisting of 0.33 mmol of 4-hydoxy-TEMPO and inhibitor-free styrene was prepared. Nine mL aliquots of this solution were charged into each of twenty-four Ace Glass #15 threaded pressure tubes equipped with PTFE screw caps and fluoroelastomer (FETFE) O-rings. The procedure in Comparative Example 4A was used to remove oxygen, polymerize the solutions, and measure the amount of polymer formed.

Example 4C

Styrene Treated with 4-benzyloxy-2,2,6,6-tetramethylpiperidin-1-ol (4-BnO-TEMPOH)

A solution consisting of 0.33 mmol of 4-benzyloxy-2,2,6,6-tetramethylpiperidin-1-ol and inhibitor-free styrene was prepared. Nine mL aliquots of this solution were charged into each of twenty-four Ace Glass #15 threaded pressure tubes equipped with PTFE screw caps and fluoroelastomer (FETFE) O-rings. The procedure in Comparative Example 4A was used to remove oxygen, polymerize the solutions, and measure the amount of polymer formed.

Example 4D

Styrene Treated with 4-butoxy-2,2,6,6-tetramethylpiperidin-1-ol (4-BuO-TMPOH)

A solution consisting of 0.33 mmol of 4-butoxy-2,2,6,6-tetramethylpiperidin-1-ol and inhibitor-free styrene was prepared. Nine mL aliquots of this solution were charged into each of twenty-four Ace Glass #15 threaded pressure tubes equipped with PTFE screw caps and fluoroelastomer (FETFE) O-rings. The procedure in Comparative Example 4A was used to remove oxygen, polymerize the solutions, and measure the amount of polymer formed.

The results of the experiments in Examples 4A-4D is summarized in Table 2:

TABLE 2

Inhibition of styrene polymerization at 120° C. under anaerobic conditions using no inhibitor (blank) or 0.33 mmol of inhibitor.

| | Polystyrene (wt. %) | | | |
|---|---|---|---|---|
| Time (min) | Ex. 4A Blank | Ex. 4B 4-OH-TEMPO | Ex. 4C 4-BnO-TMPOH | Ex. 4D 4-BuO-TMPOH |
| 30 | 1.96 | 0.03 | 0.02 | 0.004 |
| 45 | 3.24 | 0.03 | 0.02 | 0.004 |
| 60 | 4.72 | 0.04 | 0.02 | 0.003 |
| 75 | 6.36 | 0.09 | 0.02 | 0.012 |
| 90 | 7.78 | 1.93 | 2.10 | 4.00 |
| 105 | 10.57 | 7.60 | 4.28 | 7.80 |

Example 5

Polymerization of Isoprene

Comparative Example 5A

Untreated Isoprene

A disposable, prepacked alumina column was used to remove 4-tert-butylcatechol (TBC) from isoprene. Freshly de-inhibited isoprene was diluted with heptane in a 1:1 ratio. Fifty mL aliquots of this solution were charged into each of six glass sample containers, which were then placed into six stainless steel pressure vessels. Each vessel was pressurized with 100 psi nitrogen without purging the system. Polymerization reactions were carried out by loading the vessels into a heating block that had been preheated to 120° C. After 60 minutes, and every 60 minutes after that, one vessel was retrieved from the block and the polymerization reaction quenched by cooling the vessel in an ice bath. The vessels were de-pressurized and the polymer content determined gravimetrically by evaporating the volatiles at 170° C.

Comparative Example 5B

Isoprene Treated with 4-hydoxy-TEMPO (4-OH-TEMPO)

A solution consisting of 1.55 mmol of 4-hydroxy-TEMPO and inhibitor-free isoprene was prepared. The solution was diluted with heptane in a 1:1 ratio. Fifty mL aliquots of this solution were charged into each of six glass containers, which were then placed into six stainless steel pressure vessels. The procedure in Comparative Example 5A was used to remove oxygen, polymerize the solutions, and measure the amount of polymer formed.

Comparative Example 5C

Isoprene Treated with
4-benzyloxy-2,2,6,6-tetramethylpiperidin-1-ol
(4-BnO-TEMPOH)

A solution consisting of 1.55 mmol of 4-benzyloxy-2,2,6,6-tetramethylpiperidin-1-ol and inhibitor-free isoprene was prepared. The solution was diluted with heptane in a 1:1 ratio. Fifty mL aliquots of this solution were charged into each of six glass containers, which were then placed into six stainless steel pressure vessels. The procedure in Comparative Example 5A was used to remove oxygen, polymerize the solutions, and measure the amount of polymer formed.

Example 5D

Isoprene Treated with
4-butoxy-2,2,6,6-tetramethylpiperidin-1-ol
(4-BuO-TEMPOH)

A solution consisting of 1.55 mmol of 4-butoxy-2,2,6,6-tetramethylpiperidin-1-ol and inhibitor-free isoprene was prepared. The solution was diluted with heptane in a 1:1 ratio. Fifty mL aliquots of this solution were charged into each of six glass containers, which were then placed into six stainless steel pressure vessels. The procedure in Comparative Example 5A was used to remove oxygen, polymerize the solutions, and measure the amount of polymer formed.

The results of the experiments in Examples 5A-5D is summarized in Table 3:

TABLE 3

Inhibition of isoprene polymerization at 120° C. under anaerobic conditions using no inhibitor (blank) or 0.33 mmol of inhibitor.

| | Polyisoprene (wt. %) | | | |
|---|---|---|---|---|
| Time (min) | Ex. 5A Blank | Ex. 5B 4-OH-TEMPO | Ex. 5C 4-BnO-TMPOH | Ex. 5D 4-BuO-TMPOH |
| 60 | 0.5444 | 0 | 0.0036 | 0.0048 |
| 120 | 1.1616 | 0.0008 | 0 | 0.006 |
| 180 | 2.0124 | 0.01 | 0.006 | 0.0062 |
| 240 | 2.2878 | 0.0038 | 0.1628 | 0.005 |
| 300 | 2.7036 | 0.5578 | 0.6656 | 0.1648 |
| 360 | 3.308 | 1.193 | | 0.3078 |

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compounds and methods without departing from the scope of the invention, it is intended that all matter contained in the above description shall be interpreted as illustrative and not in a limiting sense.

What is claimed is:

1. A method for inhibiting polymerization of an unsaturated compound comprising an unsaturated carbon-carbon bond comprising contacting the unsaturated compound with the hydroxylamine compound of Formula 1

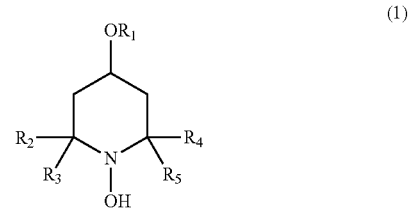

(1)

wherein
$R_1$ is alkaryl; and
$R_2$, $R_3$, $R_4$, and $R_5$, are independently alkyl.

2. The method of claim 1 wherein the unsaturated compound is a vinyl monomer.

3. The method of claim 1 wherein $R_1$ is $C_7$-$C_{18}$ alkaryl.

4. The method of claim 1 wherein $R_2$, $R_3$, $R_4$, and $R_5$, are independently $C_1$-$C_9$ alkyl.

5. The method of claim 1 wherein $R_2$, $R_3$, $R_4$, and $R_5$, are independently $C_1$-$C_3$ alkyl.

6. The method of claim 1 wherein $R_2$, $R_3$, $R_4$, and $R_5$, are independently haloalkyl.

7. The method of claim 1 wherein the unsaturated compound is ethylene, propylene, acetylene, styrene, vinyl chloride, vinyl alcohol, vinyl acetate, acrylonitrile, acrylate esters, methacrylate esters, acrylic acid, (meth)acrolein, acrolein, butadiene, indene, divinylbenzene, isoprene, acetylene, vinyl acetylene, cyclopentadiene, or a combination thereof.

8. The method of claim 7 wherein the unsaturated compound comprises acrylate esters, methacrylate esters, styrene, or a combination thereof.

9. The method of claim 1 wherein the method stabilizes and inhibits polymerization of an unsaturated compound during a manufacture, a purification, or a storage process.

10. The method of claim 9 wherein the method stabilizes and inhibits polymerization of an unsaturated compound in a primary fractionation process, light ends fractionation, non-aromatic halogenated vinyl fractionation, process-gas compression, butadiene extraction, propane dehydrogenation, diesel and petrol fuel stabilization, olefin metathesis, styrene purification, hydroxyhydrocarbon purification, or delays the polymerization of resins and compositions comprising ethylenically unsaturated species.

11. The method of claim 10 wherein the process is butadiene extraction or styrene purification.

12. The method of claim 11 wherein the unsaturated compound is a methacrylate ester.

* * * * *